(12) United States Patent
Ogilvie

(10) Patent No.: US 7,967,767 B2
(45) Date of Patent: Jun. 28, 2011

(54) METHOD AND APPARATUS FOR DYNAMIC SCOLIOSIS ORTHOSIS

(76) Inventor: James W. Ogilvie, Brighton, UT (US)

( * ) Notice: Subject to any disclaimer, the term of this patent is extended or adjusted under 35 U.S.C. 154(b) by 0 days.

(21) Appl. No.: 12/145,959

(22) Filed: Jun. 25, 2008

(65) Prior Publication Data

US 2008/0262402 A1 Oct. 23, 2008

Related U.S. Application Data

(63) Continuation-in-part of application No. 12/150,475, filed on Sep. 4, 2007, now abandoned, and a continuation of application No. 11/784,180, filed on Apr. 4, 2007, now abandoned, and a continuation of application No. 11/588,188, filed on Oct. 25, 2006, now abandoned, and a continuation of application No. 11/416,625, filed on May 2, 2006, now abandoned, and a continuation of application No. 11/261,947, filed on Oct. 28, 2005, now abandoned.

(60) Provisional application No. 60/623,073, filed on Oct. 28, 2004.

(51) Int. Cl.
*A61F 5/00* (2006.01)
*A61B 19/00* (2006.01)

(52) U.S. Cl. ............... 602/19; 602/5; 128/869

(58) Field of Classification Search ............ 602/19, 602/5, 17, 18, 36, 6, 23, 16, 28, 27; 2/44, 2/45; 128/869
See application file for complete search history.

(56) References Cited

U.S. PATENT DOCUMENTS

| | | | | |
|---|---|---|---|---|
| 2,060,173 A | 11/1936 | Buschenfeldt | | 128/78 |
| 2,687,129 A | 8/1954 | Talkish | | 128/78 |
| 3,945,047 A * | 3/1976 | Jarrell, Jr. | | 2/24 |
| 4,202,327 A | 5/1980 | Glancy | | 128/78 |
| 4,230,101 A | 10/1980 | Gold | | 128/78 |
| 4,285,336 A | 8/1981 | Oebser et al. | | 128/78 |
| 4,648,390 A | 3/1987 | Friddle | | 128/78 |
| 4,688,558 A | 8/1987 | Hooper et al. | | 128/78 |
| 4,957,103 A | 9/1990 | Young et al. | | 128/78 |
| 5,012,798 A * | 5/1991 | Graf et al. | | 602/19 |
| 5,062,415 A * | 11/1991 | Weatherby et al. | | 602/17 |
| 5,449,338 A * | 9/1995 | Trudell | | 602/19 |
| 5,474,523 A | 12/1995 | Miller | | 602/19 |
| 5,503,621 A | 4/1996 | Miller | | 602/19 |
| 5,599,286 A * | 2/1997 | Labelle et al. | | 602/19 |
| 5,599,287 A * | 2/1997 | Beczak et al. | | 602/19 |
| 5,632,724 A * | 5/1997 | Lerman et al. | | 602/19 |
| 6,080,122 A * | 6/2000 | Gulledge | | 602/16 |
| 6,676,617 B1 | 1/2004 | Miller | | 602/5 |
| 6,840,916 B2 | 1/2005 | Kozersky | | 602/19 |
| 6,932,780 B2 | 8/2005 | Kozersky | | 602/19 |
| 7,025,737 B2 | 4/2006 | Modglin | | 602/19 |

(Continued)

FOREIGN PATENT DOCUMENTS

| | | |
|---|---|---|
| JP | 2005-137448 | 2/2005 |
| KR | 20040103300 | 12/2004 |
| KR | 20040103301 | 12/2004 |
| RU | 2131713 | 6/1999 |

(Continued)

*Primary Examiner* — Patricia M Bianco
*Assistant Examiner* — Ophelia Hawthorne
(74) *Attorney, Agent, or Firm* — Michael R. Schramm

(57) ABSTRACT

The invention is a three-contact-point dynamic scoliosis orthosis (DSO) brace to aid physicians treating scoliosis. A pelvic mold and two pads, one positioned above the apex of the spine curvature, the other positioned orthogonal to the apex of the spine curvature provide the anchor points on opposite sides of the curve. The pad orthogonal to the curve's apex is adjustable.

58 Claims, 3 Drawing Sheets

U.S. PATENT DOCUMENTS

| | | | |
|---|---|---|---|
| 7,316,660 B1 | 1/2008 | Modglin | 602/5 |
| 7,322,950 B2 | 1/2008 | Modglin | 602/5 |
| 2005/0020952 A1* | 1/2005 | Pick et al. | 602/27 |
| 2005/0137508 A1 | 6/2005 | Miller | 602/19 |
| 2007/0010768 A1 | 1/2007 | Simanovsky | 602/5 |

FOREIGN PATENT DOCUMENTS

| | | |
|---|---|---|
| WO | WO9725009 | 7/1997 |
| WO | WO2005023157 | 3/2005 |
| WO | WO2006068459 | 6/2006 |

* cited by examiner

US 7,967,767 B2

METHOD AND APPARATUS FOR DYNAMIC SCOLIOSIS ORTHOSIS

CROSS REFERENCE TO RELATED APPLICATION

This nonprovisional utility patent application is a continuation-in-part of and claims the benefit under 35 USC §120 to co-pending U.S. patent application Ser. No. 12/150,475 filed Sep. 4, 2007, which is a continuation of and claims the benefit under 35 USC §120 to co-pending U.S. patent application Ser. No. 11/784,180 filed Apr. 4, 2007, which is a continuation of and claims the benefit under 35 USC §120 to co-pending U.S. patent application Ser. No. 11/588,188 filed Oct. 25, 2006, which is a continuation of and claims the benefit under 35 USC §120 to co-pending U.S. patent application Ser. No. 11/416,625 filed May 2, 2006, which is a continuation of and claims the benefit under 35 USC §120 to co-pending U.S. patent application Ser. No. 11/261,947 filed Oct. 28, 2005, which claims the benefit under 35 USC §119(e) to U.S. provisional patent application No. 60/623,073 filed Oct. 28, 2004, all of which are incorporated in their entirety by this reference with the following exception: In the event that any portion of the above-referenced applications is inconsistent with this application, this application supersedes said above-referenced applications.

FIELD OF THE INVENTION

The present invention relates to braces for use in scoliosis therapy. In particular, the present invention relates to the application of improved bracing to heal or assist in healing the scoliotic spinal curve of a patient having scoliosis.

BACKGROUND OF THE INVENTION

Apparatuses and methods for treating scoliosis have been practiced for many years. However, these generally involve heavy and bulky braces. Furthermore these braces tended to be so large and restrictive that patients had difficulty performing normal functions while wearing them, or found the braces so uncomfortable or embarrassing that patients refused to wear them.

Attempts to overcome these difficulties included cutting a hole in the brace material over the stomach to allow the wearer greater freedom to breathe. However many difficulties with the apparatus remained.

Traditional methods of using the brace are equally burdensome for users, and difficult for practitioners to implement. Braces used are not adjustable, have a closed design which increases the brace's weight and heat retention.

Furthermore, because braces are not adjustable, users have the same treatment whether asleep, when more aggressive treatment is possible, and awake, when more aggressive treatment is very painful.

SUMMARY OF THE INVENTION

The present invention teaches a method and apparatus for dynamic scoliosis orthosis. More particularly, the present invention teaches an apparatus for improving scoliosis treatment and therapy, as well as a method for making a brace and using a brace in treating patients with scoliosis.

Many other uses and advantages of the present invention will be apparent to those skilled in the art upon review of the detailed description of the preferred embodiments herein. Solely for clarity of discussion, the invention is described in the sections below by way of non-limiting examples.

DESCRIPTION OF DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE INVENTION

Figure 1:
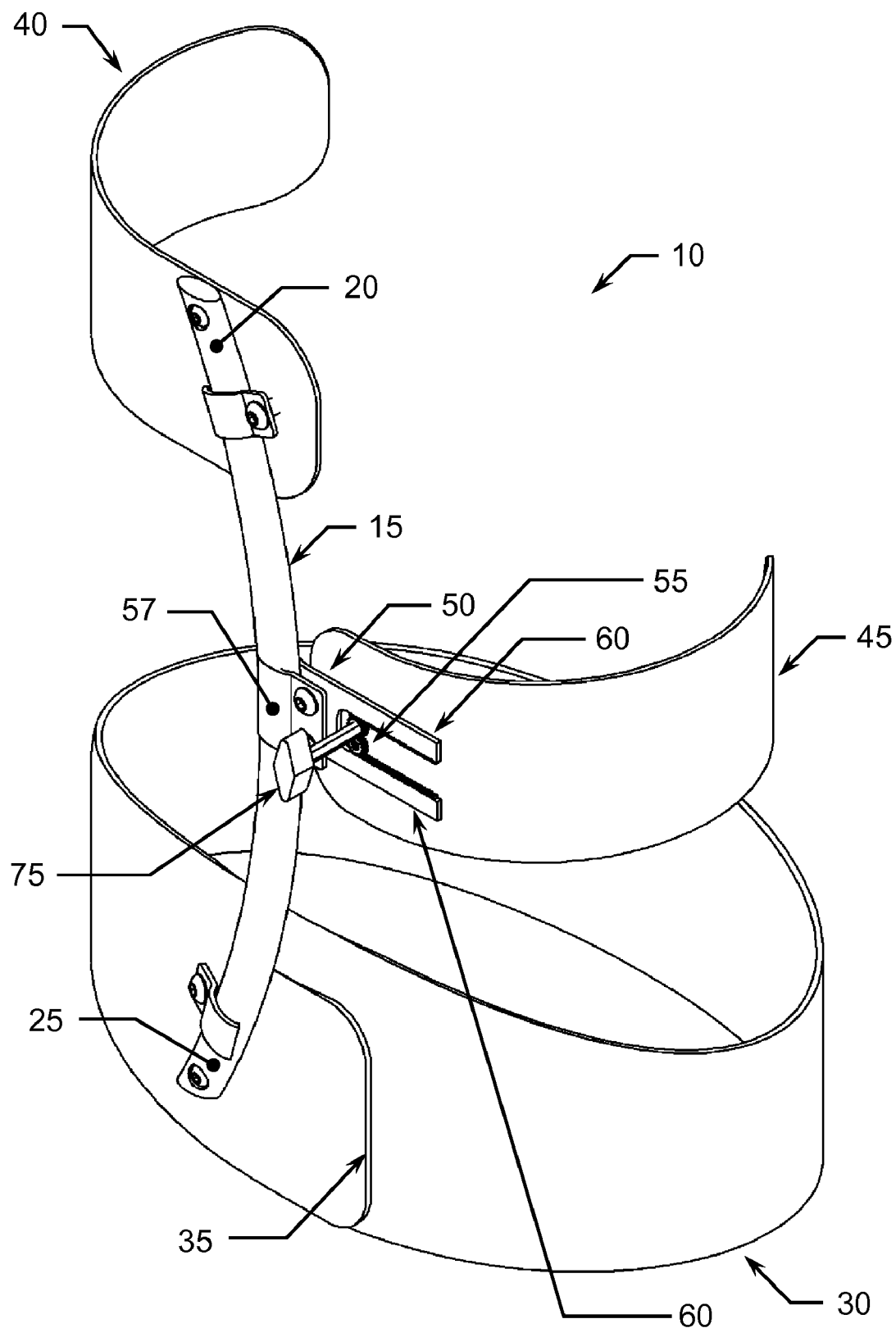
FIG. 1 is an isometric view of a first embodiment of the dynamic scoliosis orthosis (brace)
Figure 2:
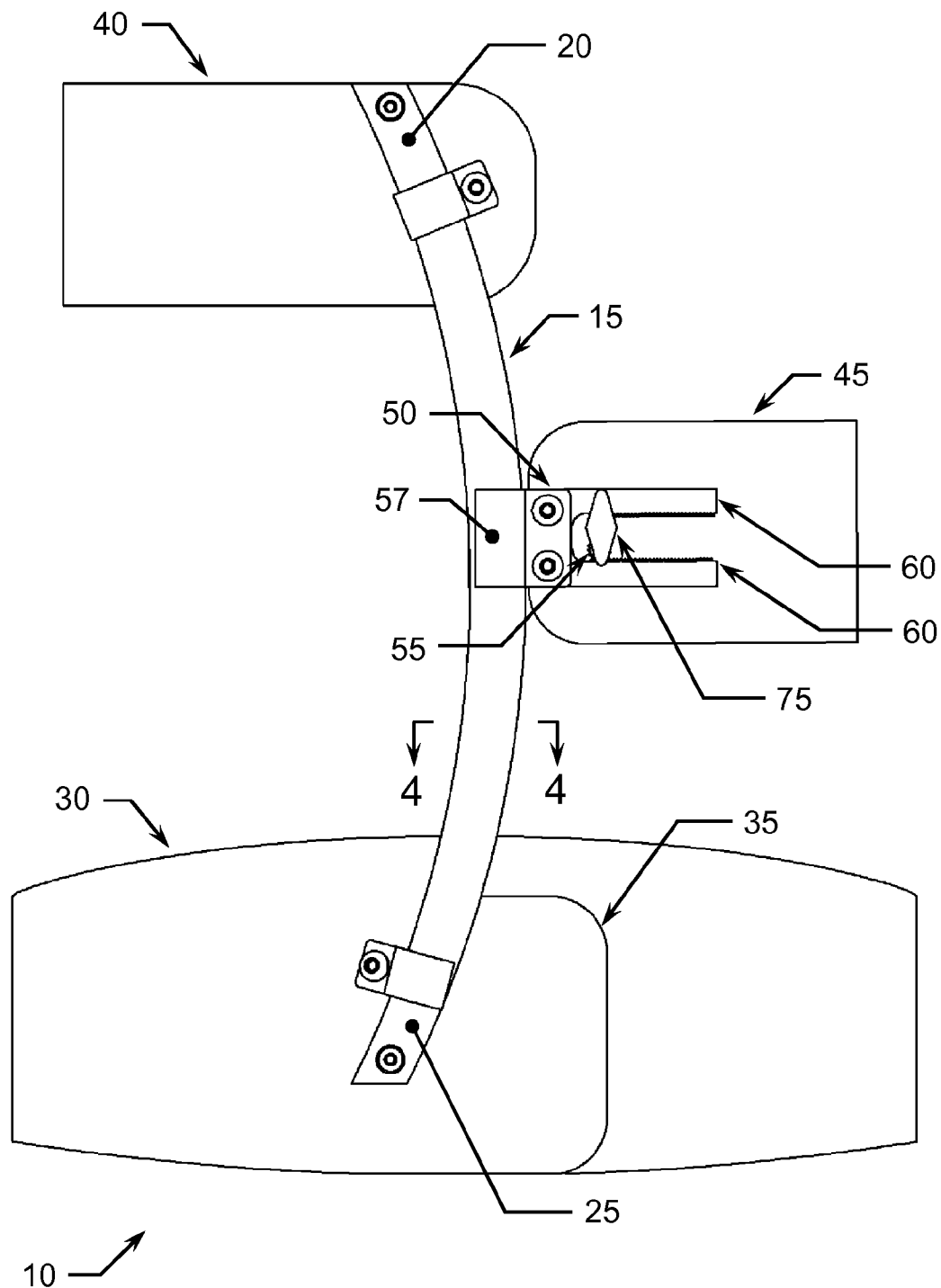
FIG. 2 is an orthographic rear view of a first embodiment of the dynamic scoliosis orthosis (brace)
Figure 3:
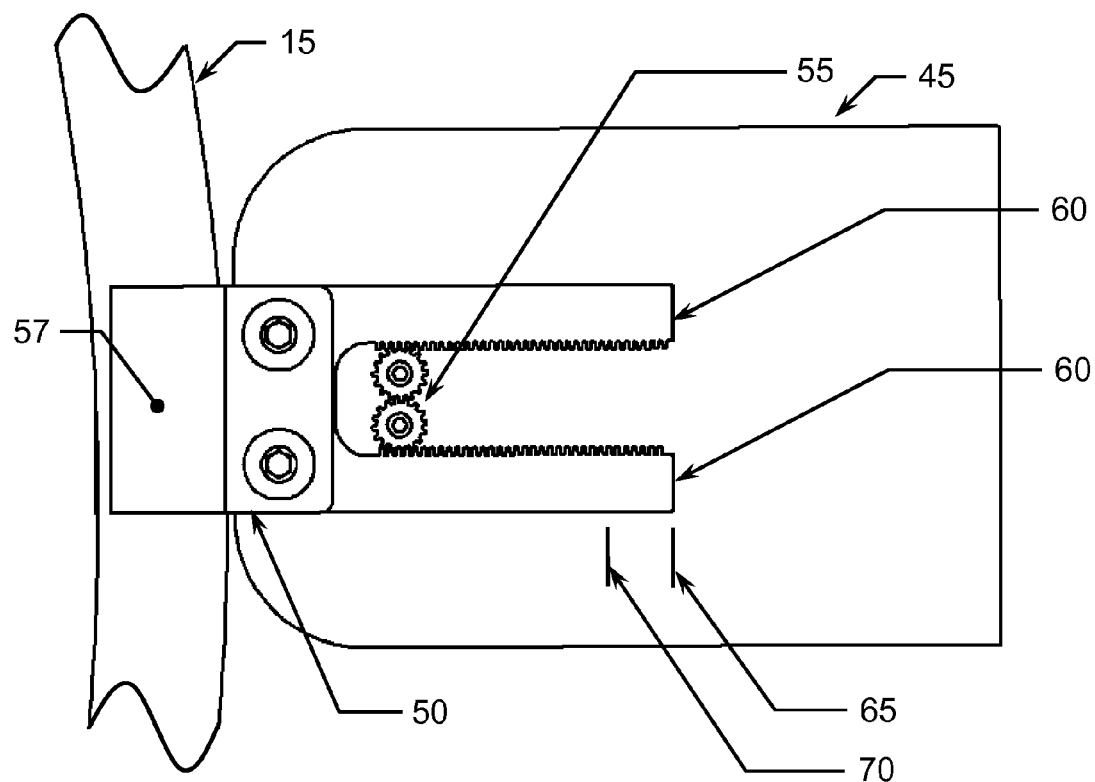
FIG. 3 is a close-up view of the apical pad portion of FIG. 2 with the adjustment key shown removed from the brace.

This specification describes exemplary embodiments and applications of the invention. The invention, however, is not limited to these exemplary embodiments and applications or to the manner in which the exemplary embodiments and applications operate or are described herein.

FIGS. 1 through 4 illustrate an exemplary embodiment of a Dynamic Scoliosis Orthosis or brace (or harness) 10. Brace 10 comprises a rod 15, a pelvic mold 30, an auxiliary pad 40, an apical pad 45, an extension arm 50, and an adjustment key 75. Rod 15 may be made of a variety of materials or composite of materials including metals such as aluminum, carbon fiber, polymers or fibers and resins. Ideally the material selected will provide a rigid and stable support for the harness, thus providing steady force on the curved spine. The exemplary embodiment of the invention teaches a carbon fiber rod because it is light weight, flexible and still extremely strong. Rod 15 has a general elliptical cross-sectional shape so as to minimize the distance that rod 15 protrudes outwardly from the user's back, and so as to provide a greater resistance to bending in a lateral or side-to-side direction than in a fore-aft direction. Such difference in the resistance to bending provides for increased flexure mobility of the user of brace 10 and yet allows brace 10 to provide substantial scoliotic correctional loading to the spine of the user of brace 10. The rod may be curved or straight, depending on what is best for the patient. The rod further comprises a first (upper) end 20 and a second (lower) end 25. The present invention further teaches treating a double curved spine by enlarging the pelvic mold so as to extend further up the user's body.

First end 20 is coupled to pelvic mold 30 which contacts the user or wearer of brace 10 below the scoliosis curve of the user. Pelvic mold 30 is preferably custom fit for each wearer, and is formed from rigid polymers such as polypropylene. The custom fit of pelvic mold 30 maximizes the effectiveness of rod 15 by providing a tight and secure anchor for rod 15. However, pelvic mold 30 may also be generically sized, and customized to fit snugly to the patient with inserts (not shown.) Inserts may also be used to improve the ease with which the present invention is cleaned. Optionally, pelvic mold 30 has a fastener 35 to aid the wearer in donning and removing the brace 10. The fastener 35 may be a belt and buckle, hook and loop, or a friction mechanism.

Auxiliary pad 40 is coupled to second end 20 of rod 15 and contacts the user or wearer's body above the scoliosis curve of the user. Generally, auxiliary pad 40 is molded so as to cup the wearer's side and apply a load in the lateral direction on the wearer's spine. Auxiliary pad 40 is preferably formed from a rigid polymer, a metal, or a composite, selecting the materials best suited for the patient's need. Auxiliary pad 40 can be permanently coupled to the rod 15 using an epoxy, a mechanical mechanism or any other means known in the art. When permanently attached to rod 15, auxiliary pad 40 preferably includes a removable and replaceable cover to improve the ease with which the pad is cleaned, replaced, or customized. However, auxiliary pad 40 may also be releasably coupled to rod 15 via a tab and sleeve configuration, or a non-permanent mechanical means known in the art. It is noted that auxiliary pad 40 may be replaced as the patient grows, or as the pad is worn out.

Extension arm 50 preferably includes an adjustment mechanism 55, adjustable mount bracket 57, guides 60, and an adjustment key 75. Extension arm 50 is adjustably coupled to the rod 15 between the ends 20 and 25 of rod 15 by means of adjustable bracket 57. Apical pad 45 is extendably and retractably coupled to extension arm 50. Apical pad 45 is similar in form and structure to auxiliary pad 40, but is positioned to create a counter force to auxiliary pad 40 on the user's spine over the apex of the curvature of the user's spine. Thus at the contact point of apical pad 45, a load is applied that is a counter load to the load applied by auxiliary pad 40 and pelvic mold 30. The amount of load exerted by apical pad 45 is adjustable via adjustment mechanism 55. Adjustment mechanism 55 may be any of a rack and pinion gear, a sliding lock, a toothed track secured by screws, or any other mechanism commonly known in the art. Removable adjustment key 75 engages into adjustment mechanism 55 and rotationally operates to adjust adjustment mechanism 55. Alternatively, a knob or like adjust device may be integrally built into adjustment mechanism 55 to operatively adjust apical pad 45. Adjustment mechanism 55 allows the user to increase the corrective load apical pad 45 exerts on the apex of the spine of the user to decrease the term of treatment of the user. Increasing the load is a common practice for patients, especially at night when the load can be greatly increased without severe discomfort to the user. Adjustment mechanism 55 is adjusted within guides 60 and according to setting marks 65 and 70. Setting mark 65 preferably corresponds to a night time tension adjustment setting and setting mark 70 preferably corresponds to a day time tension adjustment setting. Setting marks 65 and 70 are preferably placed on apical pad 45 by a physician and are placed to maximize the effectiveness of the treatment. The invention also teaches adjusting the setting to minimize the pain caused by the treatment. The extension arm 50 may be made of metal, rigid polymer or a composite material. Furthermore, extension arm 50 may be coupled to rod 15 either permanently or non-permanently by selectively using means coupling means known in the art. Finally, extension arm 50 may be adjustable on rod 15 so as to provide multiple fixation points on rod 15, thus allowing for periodic adaptation or fit of the user as the user grows. Such adaptation greatly reduces the cost of treatment by avoiding the need for the user to purchase multiple braces over time as the user grows.

Generally, because brace 10 has only three contact points, it has an open design, thus maximizing the freedom of motion of the user of the brace. The three-contact-points also minimize the amount of contact between the brace and the user, thus brace 10 is cooler and spares sensitive skin from excessive contact. For the purposes of this patent application it should be noted that the "three contact points" refer to the three principal load applying contact points. In the case of brace 10, the first principal load applied in a first substantially lateral direction by auxiliary pad 40 is applied at a first contact point. The second principal load applied in a second substantially lateral direction (substantially opposing the first lateral direction) by apical pad 45 is applied at a second contact point. And the third principal load applied in the first substantially lateral direction (substantially opposing the second lateral direction) by pelvic mold 30 is applied at a third contact point. Any other loads and load points associated with brace 10 are substantially incidental to the described scoliosis correcting principal loads and principal load points. For the purpose of defining a benefit of brace 10 disclosed herein, the amount of surface area contact of the torso of the body of the user of brace 10, the torso being understood to have an upper boundary of the user's neck and a lower boundary of the user's waist, divided by the total surface area of the torso of the body of the user of brace 10, shall be understood to be a brace to torso contact ratio. In the disclosed embodiment, the brace to torso contact ratio is no more than 60%. In alternative embodiments, the brace to torso contact ratio is no more than 50%, 45%, 40%, 35%, 30%, 25%, 20%, 15%, 10%, 5% and 3% respectively. Furthermore, the minimal nature of the invention reduces any embarrassment the user may feel because brace 10 can be concealed beneath clothing. Finally, the three-contact-points allow the wearer to breathe normally, without restricting chest expansion.

Figure 4:
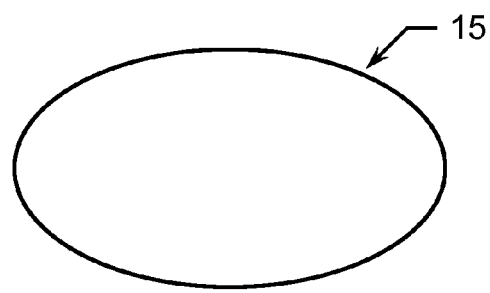
FIG. 4 is a substantially orthographic cross-sectional view of the rod portion of the brace taken at the location indicated by the section arrows in FIG. 2.

Referring now to FIG. 4, the elliptical cross-section of rod 15 functions to maximize the user's freedom of movement by allowing the user to bend forward and backward while still providing a load on the apex of the curve of the spine of the user. Brace 10 thus allows the wearer flexion and extension movements.

The modular design of brace 10 allows parts of brace 10 to be replaced and exchanged without having to replace the entirety of brace 10.

Brace 10 may be fitted to treat either a right or left curved spine.

Benefits of the dynamic scoliosis orthosis (DSO) invention include: an adjustable tension loading that allows for individualized settings for different user tolerance and for periods of low force if there is pressure sensitive skin, respiratory distress, etc., an open design that is lighter than standard thorico lubo sacral orthosis (TLSO) and results in less heat retention and greater allowable chest expansion, a provision for flexion and extension motion of the user, daytime settings that simulate a standard scoliosis TLSO and night time settings that are comparable to the Charleston nighttime brace, a modular design that allows for component replacement, and modularity and variable tension settings that permit a single orthosis to be used for the duration of brace usage resulting in cost savings. It is noted that brace 10 is primarily intended for the correction of single scoliotic curves. However, especially with the addition of an enlarged pelvic girdle, double curves (extending pelvic high) could also be treated.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An open type external brace for scoliosis therapy comprising: a structure having a first end and a second end; an auxiliary pad connected to said structure proximate said first end of said structure; a pelvic mold connected to said structure proximate said second end of said structure; and an apical pad coupled to said structure between said first end of said structure and said second end of said structure, wherein said structure defines a composite structure that includes carbon fiber and polymer, said composite structure being adapted such that the bending resistance of said composite structure in a lateral direction is greater than the bending resistance of said composite structure in a fore-aft direction, and wherein said brace includes a front portion, an aft portion, a first side, and a second side, and wherein at least one of said brace front portion and said brace aft portion is without a structure connecting said pelvic mold to either of said auxiliary pad or said apical pad, and wherein at least one of said brace first side and said brace second side is without a structure connecting said pelvic mold to either of said auxiliary pad or said apical pad.

2. The brace of claim 1, wherein said structure defines a rod.

3. The brace of claim 2, wherein said rod defines a rod having a substantially lateral plane.

4. The brace of claim 2, wherein the shape of a cross-section of said rod substantially defines an ellipse.

5. The brace of claim 2, wherein said rod defines a rod having a greater resistance to lateral bending than to non-lateral bending.

6. The brace of claim 1, wherein said brace includes an adjustment mechanism adapted to provide for lateral extension and retraction adjustment of said apical pad with respect to said structure.

7. The brace of claim 6, wherein said adjustment mechanism defines at least one of a rack and pinion adjustment mechanism, a sliding lock adjustment mechanism, and a toothed track secured by screws adjustment mechanism.

8. The brace of claim 6, wherein said lateral adjustment is made by use of a removable adjustment device.

9. The brace of claim 6, wherein said lateral adjustment includes at least two predetermined lateral adjustment settings defining a first setting and a second setting, and wherein said first setting defines a daytime adjustment setting and wherein said second setting defines a nighttime adjustment setting, and wherein said brace includes marks corresponding to said settings placed thereon.

10. The brace of claim 1, wherein a coupled location of said apical pad is adjustable between said first end of said structure and said second end of said structure.

11. The brace of claim 1, wherein at least one of said auxiliary pad, said pelvic mold and said apical pad are modular such that a first instance of at least one of said auxiliary pad, said pelvic mold and said apical pad is readily replaceable with a corresponding second instance of a respective auxiliary pad, pelvic mold and apical pad.

12. The brace of claim 1, wherein when said brace is worn by a user, said brace applies a substantially constant dynamic scoliosis corrective load on said user.

13. The brace of claim 1, wherein said brace provides for flexion and extension motion of a user of said brace.

14. The brace of claim 1, wherein said brace has no more than three principal load applying contact points.

15. The brace of claim 1, wherein said brace includes no more structures that connect said pelvic mold to either of said auxiliary pad or said apical pad than one singular structure.

16. A method of using an external brace to treat scoliosis comprising the steps of: providing an external brace, said brace comprising: a rod having a first end and a second end; an auxiliary pad connected to said rod proximate said first end of said rod; a pelvic mold connected to said rod proximate said second end of said rod; a flexible-rope-free/flexible-strap-free mechanical adjustment mechanism coupled to said rod between said first end of said rod and said second end of said rod, and an apical pad connected directly to said adjustment mechanism, and wherein said brace includes a front portion, an aft portion, a first side, and a second side, and wherein at least one of said brace front portion and said brace aft portion is without a rod, and wherein at least one of said brace first side and said brace second side is without a rod; fitting said brace to a patient with scoliosis; and treating said scoliosis by periodic brace adjustments.

17. The method of claim 16, wherein said apical pad is laterally extendably and retractably adjustable with respect to said rod.

18. The method of claim 17, wherein said lateral adjustment is made by use of a removable adjustment device.

19. The method of claim 17, wherein said lateral adjustment includes at least two predetermined lateral adjustment settings defining a first setting and a second setting, and wherein said first setting corresponds to a daytime adjustment setting and wherein said second setting corresponds to a nighttime adjustment setting.

20. The method of claim 16 wherein said method further includes the step of placing at least one adjustment mark on said brace.

21. The method of claim 20, wherein said adjustment mark defines a plurality of marks including at least a first mark and a second mark, and wherein said first mark corresponds to a daytime adjustment setting and wherein said second mark corresponds to a nighttime adjustment setting.

22. The method of claim 16, wherein said rod defines a rod having a substantially lateral plane.

23. The method of claim 16, wherein the shape of a cross-section of said rod substantially defines an ellipse.

24. The method of claim 16, wherein said rod defines a rod having a greater resistance to lateral bending than to non-lateral bending.

25. The method of claim 16, wherein a coupled location of said apical pad is adjustable between said first end of said rod and said second end of said rod.

26. The method of claim 16, wherein at least one of said auxiliary pad, said pelvic mold and said apical pad are modular such that a first instance of at least one of said auxiliary pad, said pelvic mold and said apical pad is readily replaceable with a corresponding second instance of a respective auxiliary pad, pelvic mold and apical pad.

27. The method of claim 16, wherein when said brace is worn by a user, said brace applies a substantially constant dynamic scoliosis corrective load on said user.

28. The method of claim 16, wherein said brace provides for flexion and extension motion of a user of said brace.

29. The method of claim 16, wherein said adjustment mechanism defines at least one of a rack and pinion adjustment mechanism, a sliding lock adjustment mechanism, and a toothed track secured by screws adjustment mechanism.

30. The method of claim 16, wherein said rod is comprised of at least one material defining metal, carbon fiber, polymer and a composite of at least two materials thereof.

31. The method of claim 16, wherein said brace includes no more rods than one singular rod.

32. A method of making a brace comprising: providing a rod having a lateral plane, a cross-section that substantially defines an ellipse, a first end and a second end; providing a pelvic mold having a lateral plane; providing an auxiliary pad; providing an apical pad; providing an adjustment mechanism; coupling said auxiliary pad to said rod proximate said first end of said rod, coupling said pelvic mold to said rod proximate said second end of said rod such that said lateral plane of said pelvic mold is positioned substantially coplanar to said lateral plane of said rod, coupling said adjustment mechanism to said rod between said first end of said rod and said second end of said rod, and coupling said apical pad to said adjustment mechanism.

33. The method of claim 32, wherein said apical pad is laterally extendably and retractably adjustable with respect to said rod.

34. The method of claim 33, wherein said lateral adjustment is made by use of a removable adjustment device.

35. The method of claim 33, wherein said lateral adjustment includes at least two predetermined lateral adjustment settings defining a first setting and a second setting, and wherein said first setting corresponds to a daytime adjustment setting and wherein said second setting corresponds to a nighttime adjustment setting.

36. The method of claim 32, wherein a coupled location of said adjustment mechanism is adjustable between said first end of said rod and said second end of said rod.

37. The method of claim 32, wherein said rod defines a rod having a greater resistance to lateral bending than to non-lateral bending.

38. The method of claim 32, wherein at least one of said auxiliary pad, said pelvic mold and said apical pad are modular such that a first instance of at least one of said auxiliary pad, said pelvic mold and said apical pad is readily replaceable with a corresponding second instance of a respective auxiliary pad, pelvic mold and apical pad.

39. The method of claim 32, wherein when said brace is worn by a user, said brace applies a substantially constant dynamic scoliosis corrective load on said user.

40. The method of claim 32, wherein said brace provides for flexion and extension motion of a user of said brace.

41. The method of claim 32, wherein said adjustment mechanism defines at least one of a rack and pinion adjustment mechanism, a sliding lock adjustment mechanism, and a toothed track secured by screws adjustment mechanism.

42. The method of claim 32, wherein said rod is comprised of at least one material defining metal, carbon fiber, polymer and a composite of at least two materials thereof.

43. The method of claim 32 wherein said method further includes the step of placing at least one adjustment mark on said brace.

44. The method of claim 32, wherein said brace includes no more rods than one singular rod.

45. An external brace for scoliosis therapy comprising: a rod having a first end and a second end; an auxiliary pad connected to said rod proximate said first end of said rod; a pelvic mold connected to said rod proximate said second end of said rod; a flexible-rope-free/flexible-strap-free mechanical adjustment mechanism coupled to said rod between said first end of said rod and said second end of said rod, and an apical pad connected directly to said adjustment mechanism, and wherein said brace includes a front portion and an aft portion, and wherein at least one of said brace front portion and said brace aft portion is without a rod.

46. The brace of claim 45, wherein said rod defines a rod having a substantially lateral plane.

47. The brace of claim 45, wherein the shape of a cross-section of said rod substantially defines an ellipse.

48. The brace of claim 45, wherein said rod defines a rod having a greater resistance to lateral bending than to non-lateral bending.

49. The brace of claim 45, wherein a coupled location of said adjustment mechanism is adjustable between said first end of said rod and said second end of said rod.

50. The brace of claim 45, wherein said adjustment mechanism is adjustable such that said apical pad is laterally extendably and retractably adjustable with respect to said rod.

51. The brace of claim 45, wherein said adjustment mechanism defines at least one of a rack and pinion adjustment mechanism, a sliding lock adjustment mechanism, and a toothed track secured by screws adjustment mechanism.

52. The brace of claim 45, wherein said adjustment mechanism includes at least two predetermined lateral adjustment settings defining a first setting and a second setting, and wherein said first setting defines a daytime adjustment setting and wherein said second setting defines a nighttime adjustment setting, and wherein said brace includes marks corresponding to said settings placed thereon.

53. The brace of claim 45, wherein at least one of said auxiliary pad, said pelvic mold and said apical pad are modular such that a first instance of at least one of said auxiliary pad, said pelvic mold and said apical pad is readily replaceable with a corresponding second instance of a respective auxiliary pad, pelvic mold and apical pad.

54. The brace of claim 45, wherein when said brace is worn by a user, said brace applies a substantially constant dynamic scoliosis corrective load on said user.

55. The brace of claim 45, wherein said brace provides for flexion and extension motion of a user of said brace.

56. The brace of claim 45, wherein said rod is comprised of at least one material defining metal, carbon fiber, polymer and a composite of at least two materials thereof.

57. The brace of claim 45, wherein said brace has no more than three principal load applying contact points.

58. The brace of claim 45, wherein said brace includes no more rods than one singular rod.

* * * * *